US00PP10165P

United States Patent [19]

Fear et al.

[11] Patent Number: Plant 10,165

[45] Date of Patent: Dec. 30, 1997

[54] APRICOT TREE 'SUAPRISEVEN'

[75] Inventors: Carlos D. Fear, Aptos; Bruce D. Mowrey, La Selya Beach; David W. Cain, Bakersfield, all of Calif.

[73] Assignee: Sun World, Inc., Bakersfield, Calif.

[21] Appl. No.: 694,186

[22] Filed: Aug. 8, 1996

[51] Int. Cl.[6] ..... A01H 5/00

[52] U.S. Cl. ..... Plt./39

[58] Field of Search ..... Plt./39

*Primary Examiner*—James R. Feyrer

*Attorney, Agent, or Firm*—Knobbe, Martens, Olson & Bear, LLP

[57] ABSTRACT

A new and distinct apricot tree variety characterized by its large, round fruit which exhibits a high external red blush.

1 Drawing Sheet

BACKGROUND AND SUMMARY OF THE INVENTION

This invention relates to the discovery and asexual propagation of a new variety of hybrid apricot tree, *Prunus armeniaca* cv. 'Suapriseven'. The variety produces a relatively large, round apricot, having attractive external red blush, and cultivated for the fresh fruit market. It was discovered on May 17, 1990 in Wasco, Kern County, Calif., the new variety being hybridized by Carlos D. Fear, and evaluated and selected by Bruce D. Mowrey and David W. Cain.

The variety has as its seed parent, Apricot tree cv. 'Suapritwo' (U.S. Plant Pat. No. 7,550), and its pollen parent is an unnamed, unpatented apricot tree seedling of unknown parentage and identified in the breeders' plant collection as seedling F18. The parent varieties were first crossed in February 1987, and the resulting seed was harvested and sowed in September 1987, with the date of first flowering being February 1990. The new 'Suapriseven' variety was first propagated by Bruce D. Mowrey in June 1990, in Wasco, Kern County, Calif. by budding onto Nemared rootstock.

The new variety cv. 'Suapriseven' may be distinguished from other presently available commercial apricot tree cultivars by the following combination of characteristics: the fruit of the new 'Suapriseven' apricot variety ripens early mid-season about with the Katy variety (an unpatented variety) and, thus, is usually eating ripe in Wasco, Calif. about May 18; but the 'Suapriseven' fruit can be distinguished from the Katy variety by having a larger size, more external red blush and superior eating quality.

The new variety may be distinguished from its pollen parent, seedling F18, by the following combination of characteristics: the fruit of the 'Suapriseven' has a higher external blush, improved apricot flavor and a more rounded, more desirable shape than seedling F18. The new variety may be distinguished from its seed parent, 'Suapritwo' by the following combination of characteristics: the 'Suapriseven' fruit generally ripens with the 'Suapritwo' variety and has nearly the identical appearance and eating quality as that of 'Suapritwo'; however, the new 'Suapriseven' variety is pollen fertile, whereas 'Suapritwo' is pollen sterile and requires a pollenizer. Furthermore, the 'Suapriseven' variety exhibits a more consistent bearing habit and is more productive than the 'Suapritwo' in years having a low accumulation of winter chilling hours (hours of temperatures between 32° F. and 45° F.). The new 'Suapriseven' variety has been shown to maintain its distinguishing characteristics through successive asexual propagations by, for example, budding.

BRIEF DESCRIPTION OF THE FIGURE

The accompanying drawing in FIG. 1 illustrates, in full color, a typical stem and mature leaves of the new apricot tree variety, and the outer surface of ripe fruit as viewed perpendicular to the suture line plane and looking at the suture line. The drawing also illustrates the fruit of the new variety sectioned in half from end to end, with the stone removed from the flesh.

DETAILED BOTANICAL DESCRIPTION OF THE INVENTION

Figure 1:
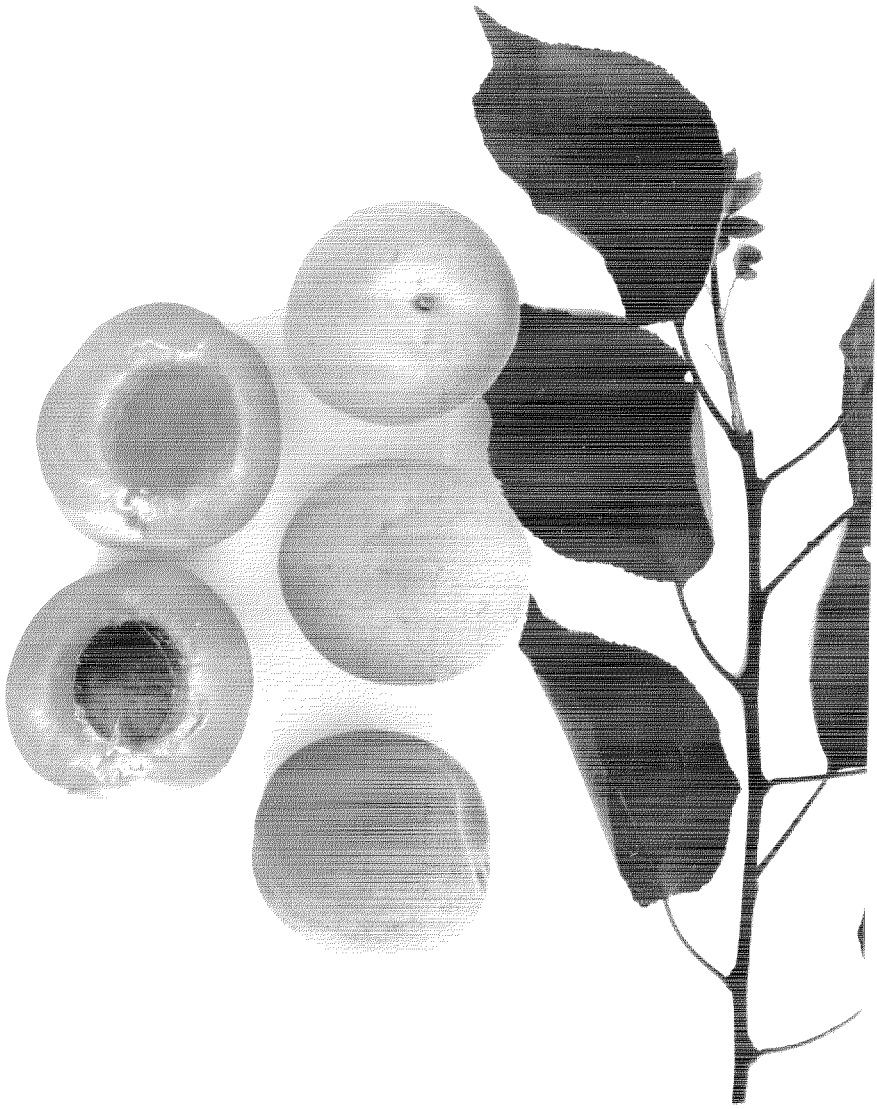

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

The descriptive matter which follows pertains to 'Suapriseven' plants grown in the vicinity of Wasco, Kern County, Calif. during 1994, and is believed to apply to plants of the variety grown under similar conditions of soil and climate elsewhere:

TREE

General:

*Size.*—Large.
*Vigor.*—Vigorous.
*Habit.*—Semi-upright.
*Density of foliage.*—Medium.
*Shape.*—Topped.
*Hardiness.*—Hardy in Wasco, Calif.
*Productivity.*—Very productive.
*Fruit bearing.*—Regular bearer.
*Root stock.*—Nemared.

Trunk:

*Shape.*—Medium to stocky.
*Surface texture.*—Medium.

Branches:

*Shape.*—Stocky.
*Surface texture.*—Medium.
*Surface appearance.*—Semi-glossy.

Lenticels:

*Number.*—Medium.
*Size.*—Large.

LEAVES

General:
*Average length.*—About 13.5 cm.
*Average width.*—About 8.25 cm.
*Size.*—Large.
*Outline.*—Spatulate.
*Profile.*—Up folded.
*Leaf blade tip.*—In the plane of the leaf.
*Angle of tip.*—Acute.
*Margin.*—Serrate.
*Undulation of margin.*—Slight.
*Apex.*—Acuminate.
*Base.*—U-shaped.
*Thickness.*—Medium.
Upper surface:
*Color.*—Green 137B.
*Glossiness.*—Weak.
*Pubescence.*—Absent.
*Surface texture.*—Smooth.
*Surface appearance.*—Dull.
Lower surface:
*Color.*—Green 137C.
*Glossiness.*—Weak.
*Pubescence.*—Absent.
*Surface texture.*—Smooth.
*Surface appearance.*—Dull.
Petiole:
*Length.*—Medium to long.
*Thickness.*—Medium.
Glands:
*Average number.*—3.
*Positioning.*—(a) On petiole; occasionally on leaf blade. (b) Alternate.
*Size.*—Medium.
*Shape.*—Globose.
*Color.*—Brown 200B.
Stipules:
*Persistence.*—Fall off.
Wood (Leaf) Buds:
*Shape.13* Rounded.
*Size.*—Very small.
*Position relative to shoot.*—Held out.
*Support.*—Not decurrent.
*Size.*—Small.
*Time of bud burst.*—Early.

FLOWERING SHOOTS

Anthocyanin coloration:
*Presence.*—Present.
*Intensity,*—Medium.
Thickness: Thick; about 1.5 cm.
Internode length: Medium; about 1.45 cm.
Buds:
*Density.*—Medium.
*Distribution.*—On spurs and one year old shoots.
*Ratio of wood (leaf) buds to flowering shoots.*—1:1.5.

FLOWERS

General:
*Date of first bloom.*—Feb. 26, 1994.
*Date of full bloom.*—Mar. 3, 1994.
*Time of bloom.*—Average, as compared with similar varieties in the growing area of Wasco, Calif.
*Duration of bloom.*—Medium.
*Size (fully opened flower).*—Medium; about 3.0 cm (diameter).
*Shape.*—Rosaceous.
*Petals.*—Overlapping.
*Color (fully opened flower).*—White 155D.
Flower-Buds:
*Hardiness.*—Hardy, in Wasco, Calif.
*Size.*—Medium.
*Length.*—Medium.
*Shape.*—Plump.
*Positioning.*—Adpressed.
*Pubescence.*—Absent.
*Color.*—Greyed-Purple 186A.
Peduncle:
*Length.*—Short.
*Thickness.*—Medium.
*Pubescence.*—Few.
Receptacle:
*Depth.*—Medium.
*Pubescence of inner surface (at white bud stage).*—Absent.
*Pubescence of outer surface.*—Few.
Sepals:
*Positioning.*—Touching receptacle.
*Shape.*—Triangular.
*Publescence of inner surface.*—Absent.
*Pubescence of outer surface.*—Few.
*Frequency of double sepals.*—Few.
Petals:
*Frequency of double petals.*—Few.
*Size.*—Medium, about 1.3 cm. in width.
*Shape.*—Transverse broad elliptic.
*Claw length.*—Short.
*Margin waviness.*—Medium.
*Base angle.*—Medium.
*Division of upper margin.*—Entire.
*Pubescence of inner surface.*—Absent.
*Pubescence of outer surface.*—Absent.
*Color.*—Inner surface: White 155D. Outer surface: White 155D.
Stigma:
*Position (as compared with anthers).*—Above.
Anthers:
*Color (just before dehiscence).*—Yellow-Orange 17B.
Pollen:
*Color.*—Yellow-Orange 14A.
Stamens:
*Position.*—Perigynous.
Pistil:
*Frequency of supplementary.*—Few.
Ovary:
*Pubescence.*—Medium.
*Density of hairs.*—Medium.
Style: style:
*Pubescence (of base).*—Medium.
*Density of hairs.*—Slight.

FRUIT

General:
*Maturity when describedl.*—Eating-ripe.
*Date.*—May 18, 1994.
*Size.*—Uniform; large.
*Axial Diameter.*—About 6 cm.
*Transverse in suture plane.*—About 5.8 cm.
*At right angles to suture plane.*—About 5.6 cm;
*Form.*—Slightly variable; oblong.

*Position of maximum diameter.*—Towards stem end.
*Symmetry about the suture.*—Asymmetric.
*Season ripening.*—Early to medium.
*Use.*—Market; fresh.
*Keeping quality.*—Good to medium.
*Resistance to.*—Insects: Good, in Wasco, Calif. Diseases: Good, in Wasco, Calif.
*Shipping quality.*—Good.

Suture: Distinct.

Ventral surface:
*Shape.*—Rounded slightly.
*Lips.*—Equal.
*Depression of apex.*—Slightly depressed.
*Pistil base.*—Persisting.
*Pubescence at apex.*—Pubescent.
*Density of apex pubescence.*—Sparse.

Stem cavity:
*Shape.*—Flaring; rounded; with suture showing on one side.
*Depth.*—About 0.8 cm.
*Breadth.*—About 2.0 cm.
*Markings.*—None.

Base:
*Shape.*—Truncate.

Apex:
*Shape.*—Rounded to truncate; slightly depressed.

Pistil Point:
*Shape.*—Apical.

Stem:
*Length.*—About 0.6 cm; medium; glabrous.
*Adherence to stone.*—Weak.

Skin:
*Thickness.*—Medium.
*Texture.*—Medium to tender.
*Reticulation.*—Absent.
*Roughness.*—Absent.
*Tenacity.*—Tenacious to flesh.
*Tendency to crack.*—Slight in wet season.
*Color.*—Orange 26A.
*Over-color (blush).*—Red 45A.
*Down (pubescence).*—Scant; does not roll up when rubbed.
*Bloom.*—Absent.

Flesh:
*Color.*—Yellow-Orange 23A.
*Surface of the pit cavity.*—yellow-Orange 23A.
*Amygdalin.*—Wanting.
*Juice.*—Moderate.
*Sugar content.*—Medium to high.
*Texture.*—Medium; melting.
*Fibers.*—Few; fine; tender.
*Ripens.*—Earliest at apex.
*Flavor.*—Vinous; excellent.
*Aroma.*—Pronounced.
*Eating quality.*—Excellent.
*Ratio of stone to flesh.*—About 5.1:109 grams.

STONE

General:
*Adherence to flesh.*—Free.
*Fibers.*—Retains short fibers; like threads along ridges.
*Size.*—Large.
*Length.*—About 3.1 cm.
*Breadth.*—About 2.8 cm.
*Width of stalk end.*—About 0.5 cm.
*Angle of stalk end.*—Obtuse.
*Thickness.*—About 1.3 cm.
*Form (profile).*—Oval; elliptical.
*Form (ventral view).*—Globular.
*Base.*—Oblique.
*Hilum.*—Narrow; oblong.
*Apex.*—Obtuse.
*Position of maximum breadth.*—Towards middle.
*Sides.*—Equal.
*Surface.*—Pitted throughout.
*Outgrowing keel.*—Absent to partly developed.
*Ridges.*—Jagged towards base.
*Pits.*—Angular.
*Ventrical edge.*—Thin; without wing toward base.
*Dorsal edge.*—Medium; with shallow, narrow groove toward base.
*Color of dry stone.*—Greyed-Orange 164C.
*Tendency to split.*—None in dry season.

We claim:

1. A new and distinct variety of apricot tree 'Suapriseven' as herein illustrated and described.

* * * * *